(12) United States Patent
Reh et al.

(10) Patent No.: US 8,557,972 B2
(45) Date of Patent: Oct. 15, 2013

(54) COMPOSITIONS AND METHODS FOR TRANSFECTION OF RNA AND CONTROLLED STABILIZATION OF TRANSFECTED RNA

(75) Inventors: Thomas A. Reh, Seattle, WA (US); Olivia M. Bermingham-McDonogh, Seattle, WA (US); Toshinori Hayashi, Yonago (JP)

(73) Assignee: University of Washington through its Center for Commercialization, Seattle, WA (US)

( * ) Notice: Subject to any disclaimer, the term of this patent is extended or adjusted under 35 U.S.C. 154(b) by 23 days.

(21) Appl. No.: 12/974,890

(22) Filed: Dec. 21, 2010

(65) Prior Publication Data

US 2011/0151557 A1 Jun. 23, 2011

Related U.S. Application Data

(60) Provisional application No. 61/288,797, filed on Dec. 21, 2009.

(51) Int. Cl.
*C07H 21/04* (2006.01)
*C12N 15/85* (2006.01)

(52) U.S. Cl.
USPC ............. 536/24.1; 435/325; 435/455

(58) Field of Classification Search
None
See application file for complete search history.

(56) References Cited

U.S. PATENT DOCUMENTS

| | | | |
|---|---|---|---|
| 5,766,891 A | 6/1998 | Shuman | |
| 5,827,657 A | 10/1998 | Hernstadt et al. | |
| 7,550,295 B2 | 6/2009 | Shuman | |

OTHER PUBLICATIONS

Russell et al., Blood, 1996. vol. 87, pp. 5314-5323.*
Batten et al (FEBS Letters, 2006. vol. 580, pp. 2591-2597).*
N. A. Bermingham, B. A. Hassan, S. D. Price et al., Science 284 (5421), 1837 (1999).
V. J. Dwarki, R. W. Malone, and I. M. Verma, Methods Enzymol 217, 644 (1993).
M. U. Ehrengruber and K. Lundstrom, Curr Protoc Hum Genet Chapter 12, Unit 12 2 (2002).
M. U. Ehrengruber and K. Lundstrom, Curr Protoc Neurosci Chapter 4, Unit 4 22 (2007).
A. Gartner, L. Collin, and G. Lalli, Methods Enzymol 406, 374 (2006).
S. P. Gubbels, D. W. Woessner, J. C. Mitchell et al., Nature 455 (7212), 537 (2008).
T. Itani, H. Ariga, N. Yamaguchi et al., Gene 56 (2-3), 267 (1987).
W. A. Keown, C. R. Campbell, and R. S. Kucherlapati, Methods Enzymol 185, 527 (1990).
R. W. Malone, P. L. Felgner, and I. M. Verma, Proc Natl Acad Sci U S A 86 (16), 6077 (1989).
R. C. Mulligan and P. Berg, Science 209 (4463), 1422 (1980).
R. C. Mulligan and P. Berg, Mol Cell Biol 1 (5), 449 (1981).
T. Mutzke, G. Schubkegel, R. Teufel et al., Nucleosides Nucleotides Nucleic Acids 24 (2), 147 (2005).
S. Perri, D. A. Driver, J. P. Gardner et al., J Virol 74 (20), 9802 (2000).
S. Sasagawa, T. Takabatake, Y. Takabatake et al., Genesis 33 (2), 81 (2002).
M. Zeitelhofer, J. P. Vessey, S. Thomas et al., Curr Protoc Neurosci Chapter 4, Unit4 32 (2009).
J. L. Zheng and W. Q. Gao, Nat Neurosci 3 (6), 580 (2000).

* cited by examiner

*Primary Examiner* — Celine Qian
(74) *Attorney, Agent, or Firm* — McDonnell Boehnen Hulbert & Berghoff LLP

(57) ABSTRACT

The present invention provides reagents and methods for RNA transfection and protein expression.

20 Claims, 10 Drawing Sheets

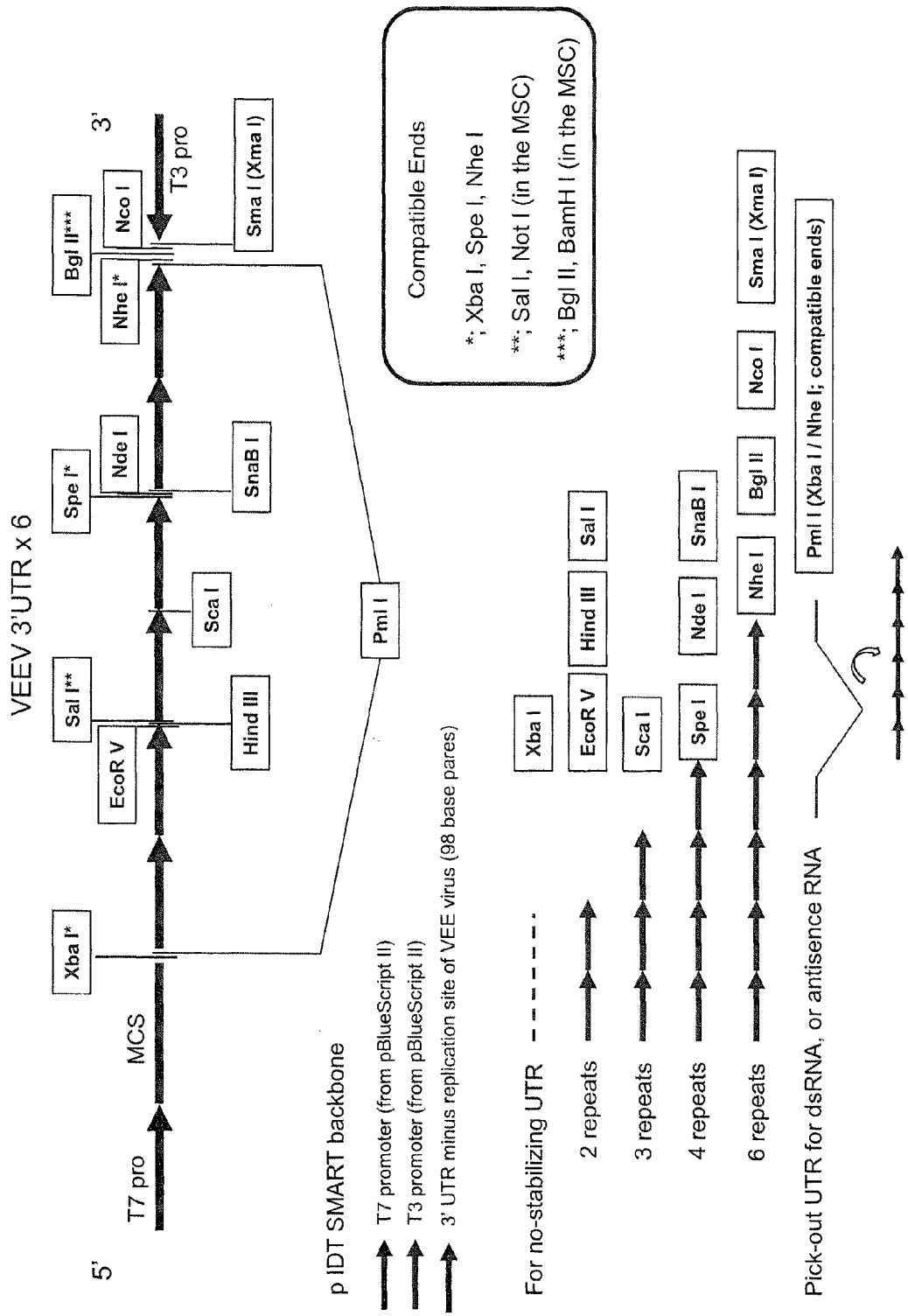
Figure 8 p Stabilizing UTR (pSLU) - Kan

Figure 9 Multiple cloning sites

Figure 10 Destabilized EGFP (d2EGFP) in pSLU
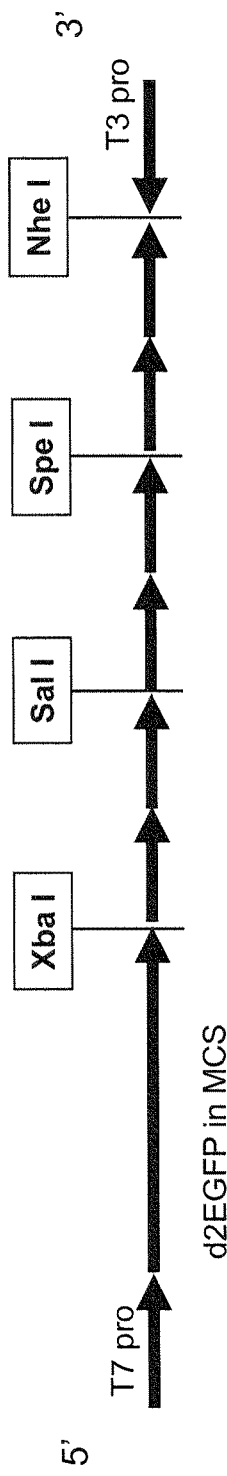
No UTR (Xba I digested) → GFP signal up to 16 hours
2 Repeats (Sal I digested) → GFP signal up to 24 hours
4 Repeats (Spe I digested) → GFP signal up to 36-48 hours
6 Repeats (Nhe I digested) → GFP signal up to 36-48 hours

US 8,557,972 B2

COMPOSITIONS AND METHODS FOR TRANSFECTION OF RNA AND CONTROLLED STABILIZATION OF TRANSFECTED RNA

CROSS REFERENCE

This application claims priority to U.S. Provisional Patent Application Ser. No. 61/288,797 filed Dec. 21, 2009, which is incorporated by reference herein in its entirety.

STATEMENT REGARDING FEDERALLY SPONSORED RESEARCH

This invention was made with U.S. government support under DC005359 awarded by the National Institutes of Health. The U.S. Government has certain rights in the invention.

TECHNICAL FIELD

The present disclosure is generally directed to nucleic acid molecules and compositions for transfection of RNA, such as mRNA, and for controlled stabilization of transfected RNA for temporally controlling expression and/or integrity of the RNA.

BACKGROUND

For many years DNA transfection has been used successfully in a large number of different cells types and tissues[1-6]. For cells that have been more difficult to transfect with DNA, viral vectors have been used for stable mis-expression[7-9]. Fewer studies have used RNA for mis-expressing genes[10-12], though studies in frog oocytes and early developmental studies have used RNA extensively, delivering it through direct microinjections. One of the reasons that RNA transfection is less widely used than DNA is its limited stability. Whereas viral mis-expression persists, potentially for the life of the cell and in dividing cells through multiple cell divisions, and plasmid transfection can persist through multiple rounds of cell division, RNA is rapidly degraded.

Nevertheless, RNA has several advantages over more traditional plasmid or viral approaches. 1. Since gene expression from an RNA source does not require transcription, the protein product is produced rapidly after the transfection, and since the mRNA has to only gain access to the cytoplasm, rather than the nucleus, typical transfection methods produce result in an extremely high rate of transfection. 2. Plasmid based approaches require that the promoter driving the expression of the gene of interest be active in the cells under study. While some of the more common promoters are active in a wide variety of cell lines, they are more limited in their expression in primary cells and tissues, particularly in post-mitotic neurons. 3. The transient nature of the expression could be useful when studying developmental processes that require only a brief "pulse" of a developmental signal or transcription factor[13].

Thus, there is a need in the art for improved reagents and methods for RNA based gene misexpression approach.

SUMMARY OF THE INVENTION

In a first aspect, the present invention provides recombinant vectors comprising (a) a transcriptional promoter;
(b) a cloning site for a gene of interest to be expressed located downstream of the transcriptional promoter; and
(c) a first recombinant nucleic acid comprising two or more copies of a polynucleotide that encodes an RNA transcript of at least a portion of a 3' untranslated region (UTR) of an RNA virus; wherein the first recombinant nucleic acid sequence is located downstream of the cloning site.

In a second aspect, the present invention provides host cells comprising the vectors of the first aspect of the invention.

In a third aspect, the present invention provides recombinant nucleic acids comprising (a) an RNA molecule; and (b) a first recombinant RNA comprising two or more copies of at least a portion of a 3' untranslated region (UTR) of an RNA virus; wherein the first recombinant RNA is coupled to the 3' end of the RNA molecule.

In a fourth aspect, the present invention provides host cells transfected with the recombinant nucleic acids of the third aspect of the invention.

In a fifth aspect, the present invention provides methods for RNA transfection, comprising transfecting a host cell with the recombinant nucleic acid of the third aspect of the invention.

BRIEF DESCRIPTION OF THE DRAWINGS

In the drawings, the sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

Figure 1:
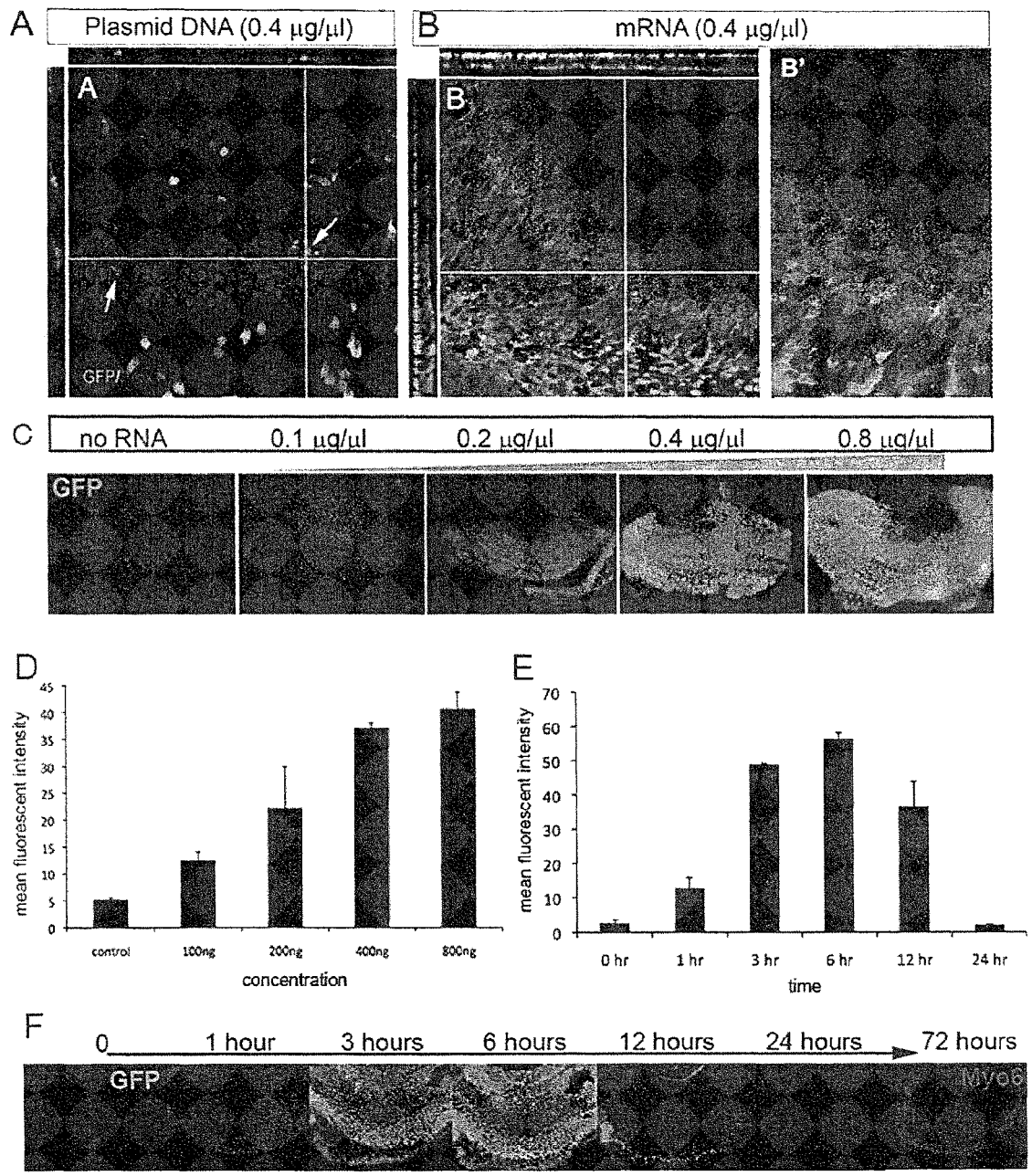
FIGS. 1A-1E demonstrate some of the differences between mRNA and plasmid cDNA transfection in the developing mouse organ of Corti. RNA can be efficiently electroporated into tissues, but expression lasts only a short time. Either plasmid DNA (A) or mRNA (B) coding for destabilized eGFP was transfected into E15 cochlear explants, and the explants fixed in paraformaldehyde either 24 hours (A) or six hours (B) later to show the difference in expression of the plasmid cDNA and mRNA transfections. The explants were immuno-labeled for Prox1 to show the sensory epithelium of the organ of Corti. The plasmid shows many GFP-expressing cells in the region adjacent to the sensory region, the greater epithelial ridge (GER) with relatively few cells within the sensory region (arrows). By contrast, the mRNA (B) shows that nearly every cell in the explant expresses GFP in both the GER and the Prox1+ sensory region. Confocal sectioning shows that many of the GFP+ cells are Prox1+ support cells. C. D. The expression of GFP in the explants correlates well with the amount of mRNA used for the transfection, from 0.1 ug/ul to 0.8 ul/ug, where it begins to plateau. E.F. The transient nature of the mRNA-induced expression is seen when the same explant is imaged live at intervals of 1, 3, 6, 12, 24 and 72 hours after the transfection. Expression of GFP can already be observed as early as 1 hour post-transfection (F, E), and this peaks between 3 hrs and 6 hrs. There is a noticeable decline in the level of GFP at 12 hours and by 24 hours is has declined to pre-transfection levels. Myosin6 (Myo6) was used to label the explant after fixing at 72 hours to show the sensory epithelium is maintained throughout this period.

and demonstrate stabilization of mRNA for longer periods of time in cells in accordance with one embodiment of the disclosure. The pSLU plasmid incorporates sequences from the VEEV 3'UTR to stabilize mRNA for longer periods in cells. (A) The pSLU plasmid was designed to allow different numbers of UTR repeats, depending on the restriction digestion for preparing the template. (B) mRNA synthesized from the templates prepared with one of four different restriction enzymes shows that the message has the appropriate length for multimers of the VEEV sequences. (C,D) Cochlear explants were transfected with mRNA with either no VEEV sequences (Xba1), 4 repeats (Sal1) or 6 repeats (Nhe1) and the level of GFP expression analyzed at 6, 12, 24, and 36 hours after transfection. GFP expression is robust in all at 6 hours, but with no VEEV sequences expression is absent at 12 hours. With either 4 or 6 repeats, expression is strong (approximately 50% of the 6 hr level) at 24 hours and still apparent at 36 hours. Note in all experiments, destabilized eGFP is used to prevent persistence of the GFP protein after the message has been degraded. (E,E') The mRNA is functional in an assay of hair cell production in the cochlea. GFI, a marker of hair cells is expressed in the sensory epithelium of the cultures (arrows) similar to that of myo6 in earlier panels. When Atoh1 mRNA is transfected into the explants, there is a large increase in the number of GFI+ hair cells (arrowheads) throughout the GER (E').

FIGS. 3A-3J demonstrate expression of pSLU plasmid mRNA coding for the transcription factor Ascl1 in the embryonic retina in accordance with one embodiment of the disclosure. mRNA coding for the transcription factor ASCl1 was transfected along with mRNA for GFP into embryonic retina, either as a plasmid (A, B, E, E') or as stabilized mRNA made from the six repeat form of pSLU (C, D, F, F'). The retinal explant was allowed to survive in vitro for 24 hours and then the level of Ascl1 expression was assessed with an antibody against Ascl1. The plasmid transfection results in scattered cells throughout the retina expressing both GFP (A, E) and Ascl1 (B, E'), the latter clearly expressed above the labeling of endogenous Ascl1 (E). However, mRNA transfection results in nearly every cell expressing high levels of both Ascl1 (D, F') and GFP (C, F). This level of expression was quantified for the plasmid transfection in G for GFP and H for Ascl1, by taking a profile of a single line across the field shown in A. Note the correspondence between the peak for GFP and Ascl1 in G and H. However, panels I and J show the much broader and higher efficiency of transfection, as well as co-expression achieved with mRNA (not the scale changes in panel J from H).

FIGS. 4A-4F demonstrate expression of pSLU plasmid mRNA coding for destabilized eGFP in neurons derived from human ES cells in accordance with one embodiment of the disclosure. mRNA for GFP was transfected into embryonic mouse cerebral cortex in vitro (B, C, E, F) while the panels in A and D show an untransfected cortical slice from the same mouse. Panels C and F show higher magnification views of B and E. Expression of the transfected GFP mRNA was highest in the upper layers of the cortex, where the neurons were layering. Labeling the explants with the neuron-specific antibody TuJ1 (anti-beta III tubulin) shows that cortical neurons can be transfected with this method and express the stabilized mRNA.

FIGS. 5A-5D demonstrate expression of pSLU plasmid mRNA coding for destabilized eGFP in neurons derived from mouse cerebral cortex in accordance with one embodiment of the disclosure. Human embryonic stem cells were used to generate retinal neurons and then transfected by electroporation with a stabilized GFP mRNA with six repeats made from pSLU (A, C, D) after 48 hours. Panels C and D show the same field, showing that many of the transfected cells expressing GFP are TuJ1+retinal neurons.

Figure 6:
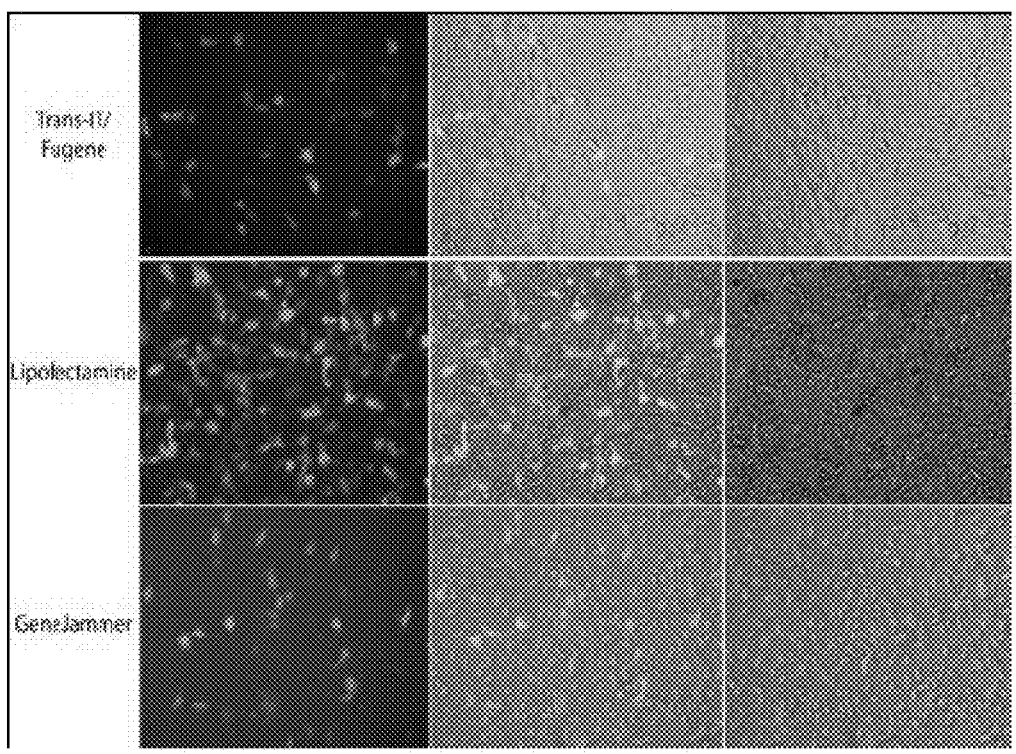

FIG. 6 demonstrates expression of pSLU plasmid mRNA coding for destabilized eGFP in a human embryonic kidney (HEK) cell line in accordance with one embodiment of the disclosure. HEK cells were transfected with stabilized GFP mRNA made from the 6 repeat form of pSLU using different lipid-based transfection reagents. TRANS-IT/FUGENE® (Roche), LIPOFECTAMINE® (Invitrogen) and GENEJAMMER® (Agilent) were all effective in RNA transfections in HEK cells to varying degrees when used according to the manufacturers' directions.

Figure 7:
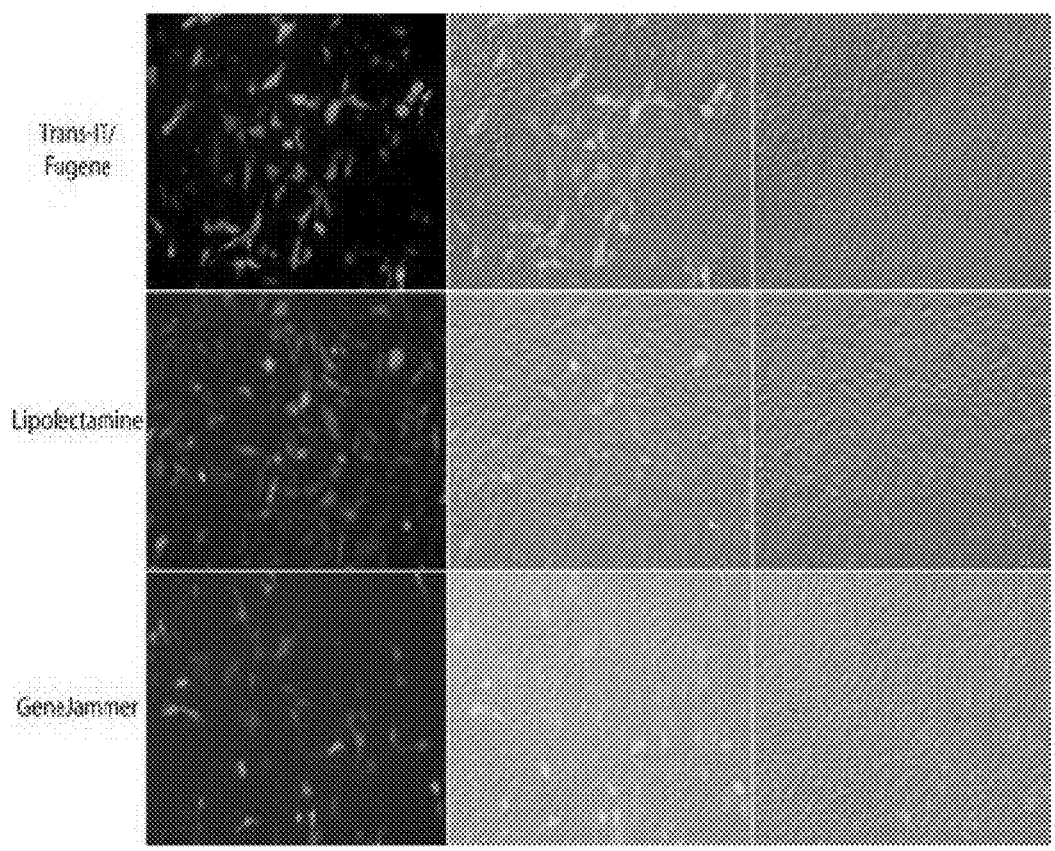

FIG. 7 demonstrates expression of pSLU plasmid mRNA coding for destabilized eGFP in an immortalized Muller glial cell line in accordance with one embodiment of the disclosure. Cells from a Muller glial cell line were transfected with stabilized GFP mRNA made from the 6 repeat form of pSLU using different lipid-based transfection reagents. TRANS-IT/FUGENE® (Roche), LIPOFECTAMINE® (Invitrogen) and GENEJAMMER® (Agilent) were all effective in RNA transfections in Muller glial cells to varying degrees when used according to the manufacturers' directions.

FIG. 8 illustrates a linear map of a Stabilizing UTR (pSLU) plasmid having a multimer of a sequence coding for the 3'UTR of Venezuelan equine encephalitis virus (VEEV) in accordance with one embodiment of the disclosure.

FIG. 9 illustrates a linear map of a pSLU plasmid and showing multiple restriction enzyme recognition sites for cloning nucleic acid sequence in accordance with one embodiment of the disclosure.

FIG. 10 illustrates a linear map of a pSLU plasmid containing mRNA coding for GFP cloned into the multiple cloning site (MCS) region in accordance with one embodiment of the disclosure, and shows a summary of the results obtained with transfection of primary cells with different lengths of the VEEV stabilizing sequences.

DETAILED DESCRIPTION

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides recombinant vectors comprising:

(a) a transcriptional promoter;

(b) a cloning site for a gene of interest to be expressed located downstream of the transcriptional promoter; and (c) a first recombinant nucleic acid comprising two or more copies of a polynucleotide that encodes an RNA transcript of at least a portion of a 3' untranslated region (UTR) of an RNA virus; wherein the first recombinant nucleic acid sequence is located downstream of the cloning site.

The inventors have discovered that incorporating two or more copies of a polynucleotide that encodes an RNA transcript of at least a portion of a 3' (UTR) of an RNA virus (ie: "stabilizing sequence") unexpectedly serves to stabilize mRNA expressed from the gene of interest in a predictable manner. As shown in the examples that follow, transfection into cells of RNA expressed using the vectors of the invention results in rapid translation in vivo, with expression observed after only an hour. Since no in vivo transcription is necessary, protein expression is similar regardless of the cell type and no cell-specific promoters are needed. In addition, the protein expression is transient, but by incorporating different numbers of encoded stabilizing sequences in the vector, the duration of in vivo protein expression from transfected RNA can be varied from as desired for a given purpose. The ability to express proteins in vivo transiently but efficiently for specific lengths of time from RNA expressed using the vectors if the invention is valuable for a variety of applications, such as therapeutic uses and studies of developmental and a wide variety of other processes. The recombinant vectors can also be used, for example, to prepare RNA-based fusions (including but not limited to siRNA, shRNA, RNA vaccines, miRNA, etc fused to the stabilizing sequences.) for delivery via RNA transfection, such as for transfection of RNA-based therapeutics.

As used herein, the first nucleic acid is "recombinant" in that it is from a different source than (a) vector, and (b) promoter. The "polynucleotide that encodes an RNA transcript of at least a portion of a 3' (UTR) of an RNA virus", also referred to herein as "stabilizing sequence" can be derived from any RNA virus. In one embodiment, the multiple copies of the stabilizing sequence are all derived from the same RNA virus; in other embodiments, the multiple copies are derived from two or more different RNA viruses. In one preferred embodiment, the stabilizing sequences are derived from Venezuelan equine encephalitis virus (VEEV) and/or Sindbis virus (SV). In further preferred embodiments, the stabilizing sequence comprises or consists of two or more copies of SEQ ID NO:1 and/or SEQ ID NO:2.

The first recombinant nucleic acid comprises two or more copies of the stabilizing sequence. Thus, in various embodiments, the first recombinant nucleic acid comprises 2, 3, 4, 5, 6, 7, 8, 9, 10, or more copies of the stabilizing sequence. The stabilizing sequence will be operatively coupled to the 3' end of a RNA product expressed from a gene of interest cloned into the cloning site after RNA expression from the vector. As will be understood by those of skill in the art, the multiple copies of the stabilizing sequence do not have to be contiguous and may contain sequences in between the copies. Such "intervening sequences" may be of any length suitable for a given vector and desired use. In one non-limiting embodiment described below, such intervening sequences may comprise restriction enzyme recognition sequences, to facilitate production of vectors with a desired number of encoded stabilizing sequences.

In a preferred embodiment, the first recombinant nucleic acid comprises 3 or more copies of the stabilizing element, wherein the first recombinant nucleic acid further comprises one or more unique restriction enzyme sites located between copies two and three of the polynucleotide. In this embodiment, the presence of the one or more unique restriction sites between copies two and three of the stabilizing sequence permits a user to "tune" the vector to produce RNA transcripts that, when transfected into cells, express protein for a desired period of time, as discussed in more detail below. As will be understood by those of skill in the art, one or more restriction sites can be placed between the second and third copies, the third and fourth copies, the fourth and fifth copies, the fifth and sixth copies, the sixth and seventh copies, the seventh and eighth copies, etc., of the stabilizing sequence, to provide a vector that permits a wide variety of options for appropriately tuning the in vivo stability of RNA transcripts produced from the vector.

The "cloning site" can be any suitable sequence element for cloning of a gene of interest. In one non-limiting embodiment, the cloning site comprises one or more restriction enzyme sites unique in the vector, in which the gene of interest can be cloned. In one embodiment, the vector comprises a plasmid, and the cloning site comprises a sequence coding for the lacZ α-peptide, interrupted by one or more unique restriction enzyme sites. After cloning, recombinant plasmids can be selected by color screening as is well known in the art.

In another embodiment, the cloning site can comprise at least a first and a second recombination site that do not recombine with each other flank an insertion site, for recombinational cloning. As used herein, a "recombination site" is a discrete section or segment of DNA that is recognized and bound by a site-specific recombination protein during the initial stages of integration or recombination. Exemplary recombination sites include, but are not limited loxP, psi, cer, attB, attP, attL, and attR sequences, and mutants, variants or derivatives. In another embodiment, the cloning site is designed for topoisomerase-mediated cloning, as described in U.S. Pat. Nos. 5,766,891 and 7,550,295, and/or TA cloning, as disclosed in U.S. Pat. No. 5,827,657, both references incorporated by reference herein in their entirety.

Any suitable transcriptional promoter that can direct in vitro RNA synthesis can be used. The term "promoter" includes any nucleic acid sequence sufficient to direct transcription in the host cell, including inducible promoters, repressible promoters and constitutive promoters. In one preferred embodiment the vector is used for in vitro RNA expression to generate RNA that can be used to transfect cells of interest. In this embodiment, any promoter that can be used for in vitro transcription can be used, including but not limited to a T3 promoter, a T7 promoter, and an SP6 promoter.

Any suitable double stranded DNA vector that can support in vitro RNA transcription can be used. The vector can be circular or linear, and may comprise any type of vector, including but not limited to plasmid vectors, viral vectors, shuttle vectors for use in different hosts, mutagenesis vectors, transcription vectors, etc. Exemplary vectors include pcDNA II, pSL301, pSE280, pSE380, pSE420, pTrcHisA, B, and C, pRSET A, B, and C (Invitrogen Corp., Carlsbad, Calif.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Invitrogen Corp., Carlsbad, Calif.) and variants and derivatives thereof. Destination Vectors can also be made from eukaryotic Expression Vectors such as pFastBac, pFastBac HT, pFastBac DUAL, pSFV, and pTet-Splice (Invitrogen Corp., Carlsbad, Calif.), pEUK-C1, pPUR, pMAM, pMAM-neo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSGS, pPbac, pMbac, pMC1neo, and pOG44 (Stratagene, Inc.), and pYES2, pAC360, pBlueBacHis A, B, and C, pVL1392, pBsueBacIII, pCDM8, pcDNA1, pZeoSV, pcDNA3 pREP4, pCEP4, and pEBVHis (Invitrogen Corp., Carlsbad, Calif.), pUC18, pUC19, pBlueScript, pSPORT, cosmids, phagemids, YACs (yeast artificial chromosomes), BACs (bacterial artificial chromosomes), MACs (mammalian artificial chromosomes), pQE70, pQE60, pQE9 (Quiagen), pBS vectors, PhageScript vectors, BlueScript vectors, pNH8A, pNH16A, pNH18A, pNH46A (Stratagene), pcDNA3 (Invitrogen, Carlsbad, Calif.), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Invitrogen Corp., Carlsbad, Calif.) and variants or derivatives thereof.

The vectors of the invention can comprise any other functional components as desirable for a given purpose, including but not limited to origins of replication (prokaryotic, and/or eukaryotic, for amplification of the vectors; viral for preparation of single stranded DNA), transcriptional enhancer elements, transcriptional termination signals, polyadenylation sequences (located 3' to the translation stop codon), sequences for optimization of initiation of translation (located 5' to the coding sequence), translation termination sequences, selectable markers (such as antibiotic resistance, lacZ coding regions, etc.), sequences that direct post-translational modification (e.g., glycosylation sites), etc. In one embodiment, a vector according to the present invention contains a stretch of dA:dT residues at one end of the cloning site. This allows the in vitro synthesis of RNA containing a synthetic 30-base poly(A) tail.

In another embodiment, the vectors contain opposed, different promoters (such as SP6 and T7 promoters) flanking the cloning site, allowing RNA to be transcribed from either strand of the insert. In this embodiment, stabilization sequences can be encoded on both strands of the vector, downstream of the cloning site.

In a further embodiment, that can be combined with any of the other embodiments herein, the recombinant vector further comprising a recombinant nucleic acid insert cloned into the cloning site, wherein the cloned recombinant nucleic acid insert is operatively linked to the transcriptional promoter and the first recombinant nucleic acid. As used herein, "operatively linked" means capable of effecting the expression (promoter) or stability (first recombinant nucleic acid) of the nucleic acid molecules. The promoter and first recombinant nucleic acid need not be contiguous with the nucleic acid insert, so long as they function to direct the expression or stability thereof. Any recombinant nucleic acid insert of interest can be cloned into the cloning site. Exemplary such inserts are those that are to be expressed as RNAs for subsequent transfection into a host cell of interest.

In a second aspect, the present invention provides host cells comprising the recombinant vectors of any embodiment of combination of embodiments of the invention. Such host cells can be of prokaryotic or eukaryotic, including but not limited to bacterial (such as *E. coli*), algal, fungal (such as yeast), insect, invertebrate, plant, and mammalian cell types. For examples of such hosts, see Maniatis et al., Molecular Cloning: A Laboratory Manual, Cold Spring Harbor Laboratory, Cold Spring Harbor, N.Y. (1982). Such host cells can be used, for example, to produce large quantities of the vector. Production of such host cells is well within the level of skill in the art based on the teachings herein.

In a third aspect, the present invention provides recombinant nucleic acids, comprising (a) an RNA molecule; and (b) a first recombinant RNA comprising two or more copies of at least a portion of a 3' untranslated region (UTR) of an RNA virus, wherein the first recombinant RNA is coupled to the 3' end of the RNA molecule.

The recombinant nucleic acids of this third aspect can be used, for example, to transfect cells of interest for protein expression, and to stabilize the RNA molecule in a cell, for example, to increase the half life of the RNA molecule in the cell. The recombinant nucleic acids of this third aspect can be made, for example, by in vitro transcription from the recombinant vectors of any embodiment or combination of embodiments of the first aspect of the invention in which a recombinant nucleic acid insert is cloned into the cloning site. In vitro transcription assays are well known to those of skill in the art. For example, a DNA vector according to any embodiment or combination of embodiments of the invention is purified and linearized at an appropriate restriction site prior to the transcription reaction to generate the template for a RNA transcript of interest, whether containing 2, 3, 4, 5, 6, 7, 8, 9, 10, or more copies of the stabilization sequence. Transcription of RNA can be performed with the appropriate RNA polymerase (T3, T7 or SP6), depending on the RNA polymerase promoter sites present in the vector used, in the presence of ribonucleotide triphosphates, a buffer system that includes DTT and magnesium ions, and an appropriate phage RNA polymerase. The exact conditions used in the transcription reaction depend on the amount of RNA needed for a specific application.

The "two or more copies of at least a portion of a 3' untranslated region (UTR) of an RNA virus" (stabilizing sequence) of this third aspect can be derived from any RNA virus as discussed above. In one embodiment, the multiple copies of the stabilizing sequence are all derived from the same RNA virus; in other embodiments, the multiple copies are derived from two or more different RNA viruses. In one preferred embodiment, the stabilizing sequences are derived from Venezuelan equine encephalitis virus (VEEV) and/or Sindbis virus (SV). In further preferred embodiments, the stabilizing sequence comprises or consists of two or more copies of SEQ ID NO:1 and/or SEQ ID NO:2. The stabilizing sequence comprises two or more copies of the stabilizing sequence. Thus, in various embodiments, the first recombinant RNA comprises 2, 3, 4, 5, 6, 7, 8, 9, 10, or more copies of the stabilizing sequence. As will be understood by those of skill in the art, the RNA molecule and the two or more stabilizing sequences do not have to be contiguous and may contain intervening sequences. Such intervening sequences may also be present between copies of the stabilizing sequence. Such "intervening sequences" may be of any length suitable for a given recombinant nucleic acid and desired use.

The RNA molecule of the recombinant nucleic acids of this aspect of the invention may be any suitable RNA molecule, particularly RNA molecules to be transfected into a host cell for a desired purpose, such as for protein expression analysis, RNA-based therapeutics, etc. In one embodiment, the RNA molecule is an mRNA molecule, and the stabilization sequence is effective to increase the period of translation of the mRNA molecule in a cell after transfection. In another embodiment, the RNA molecule is an siRNA molecule, or in further embodiment, an miRNA mimic molecule.

The RNA molecule and stabilizing sequences are coupled via any suitable means, preferably covalently coupled, such as by one or more phosphodiester bonds. The recombinant nucleic acid may include other components, such as labels for imaging in cells, transduction domains to facilitate crossing of cell membranes, etc. The recombinant nucleic acid may be present in a composition comprising a solvent, such as a pharmaceutically acceptable carrier; liposomes; transfection buffer; etc.

In a fourth aspect, the present invention provides host cells transfected with the recombinant nucleic acids of the third aspect of the invention. Such host cells can be of prokaryotic or eukaryotic, including but not limited to bacterial (such as E. coli), algal, fungal (such as yeast), insect, invertebrate, plant, and mammalian cell types. For examples of such hosts, see Maniatis et al., Molecular Cloning: A Laboratory Manual, Cold Spring Harbor Laboratory, Cold Spring Harbor, N.Y. (1982). Such host cells can be used, for example, in developmental and other cell-based studies. Production of such host cells is well within the level of skill in the art based on the teachings herein.

In a fifth aspect, the present invention provides methods for RNA transfection, comprising transfecting the recombinant nucleic acid of claim of any embodiment or combination of embodiments of the third aspect of the invention into a host cell. RNA can be delivered to cells by a variety of means including microinjection, electroporation, and lipid-mediated transfecti Such methods can be used, for example, for developmental or other studies on protein expression. In some embodiments, the cell target of RNA transfection can be a clinical target for which stabilized RNA is transfected for eliciting a therapeutic effect in the clinical target. In yet a further embodiment, the hybrid nucleic acid molecule described herein can be used to generate induced pluripotent stem cells (iPS cells). For example, hybrid nucleic acid molecules providing translatable RNA sequence for stabilized expression of transcription factors (e.g., Oct 4, c-Myc, Sox2, Klf4) can be transfected into target cells.

Polyadenylated mRNAs undergo multiple rounds of translation, but with each round, deadenylases shorten the polyA tail. Once the tail is removed, the mRNA is degraded from the 3' end via the exosome. The methods of the present invention utilize RNA, such as mRNA with increased stability by slowing their degradation after transfection. Resulting protein expression is transient, but by incorporating different numbers of encoded stabilizing sequences in the recombinant nucleic acid, the duration of in vivo protein expression from transfected RNA can be varied from as desired for a given purpose.

FIG. 1 demonstrates some of the differences between mRNA and plasmid cDNA transfection in the developing mouse organ of Corti, a tissue that has proven difficult to transfect with existing methods. A typical example of a plasmid DNA transfection by electroporation in the embryonic organ of Corti is shown in FIG. 1 A. Scattered cells express the GFP in regions adjacent to the sensory region, but few cells express GFP in the sensory region, which is labeled with Prox1 (red). By contrast, when mRNA is transfected using the same electroporation method in a sister explant, instead of a few scattered cells, nearly every cell in the explant expresses some level of GFP (FIG. 1 B). It is difficult to make out the individual cells in these explants since the GFP expression is so widespread, however, the confocal sectioning Z-axis reconstructions show that the cells with the highest levels of expression in the Prox1+ region are likely support cells, though hair cells may also express the GFP. A higher magnification image of this region shown in FIG. 1B' also confirm the most Prox1+ cells express GFP. The "dose-response" of the expression of GFP from the mRNA is shown in a series of micrographs taken of other transfected cochlear explants (FIG. 1 C). The level of GFP expression directly correlates with the amount of mRNA used in the electroporation. However, when we analyzed the time course of expression of the GFP, using a destabilized eGFP so that persistence of the GFP does not affect our interpretation of message stability, we find that while expression is rapid, with protein already visible at 1 hour and the level peaks around 6 hours, it is noticeably reduced by 12 hours and no longer detectable by 24 hours. These data show that mRNA transfection is an extremely efficient approach for gene mis-expression, even in tissue that have proven difficult to transfect with plasmid based approaches, but that the mis-expression is highly transient.

EXAMPLES

The following examples are intended to demonstrate aspects of the disclosure more fully without acting as a limitation upon the scope of the disclosure, as numerous modifications and variations will be apparent to those skilled in the relevant art.

Synthesis of pSLU Vector

The DNA coding viral 3'UTRs were synthesized and sub-cloned into pIDT SMERT v3 by Integrated DNA technologies, Inc. (Coralville, Iowa) (FIG. 8). The sequences of Sindbis viral 3' UTR and VEEV were obtained from NCBI data base (Sindbis virus; U90536.1, nucleotides 3793 to 4092: VEEV; NC_001449.1, nucleotides 11330 to 11427). Both sequences are lacking a 19-nucleotide conserved sequence element (3' CSE) which is crucial for the duplication of the viral RNA. For construction of pSLU, the DNA coding T7 promoter, a multiple cloning site, 6× VEEV 3' UTR and a T3 promoter were synthesized by Integrated DNA technologies, and then, sub-cloned into pIDT SMERT v3 (see Table 1). The genes of interest were sub-cloned into the multiple cloning site (FIG. 9) of pSLU by BamHI/XbaI (d2EGFP; Clonethech) or EcoRI/XbaI (Mash1 and Math1).

TABLE 1

| SEQ ID NO. | FRAGMENT | LENGTH |
|---|---|---|
| 1 | VEEV 3'UTR | 98 nucleotides |
| 2 | Sindbis 3'UTR | 300 nucleotides |
| 3 | pSLU Cassette (exemplary 6-repeat backbone that can be cloned into any suitable vector) | 790 nucleotides |
| 4 | T7 promoter sequence in SEQ ID NO. 3 TAATACGACTCACTATAGGGC | 21 nucleotides |

TABLE 1-continued

| SEQ ID NO. | FRAGMENT | LENGTH |
|---|---|---|
| 5 | T3 promoter sequence in SEQ ID NO. 3<br>CCCTTTAGTGAGGGTTAATT | 20 nucleotides |
| 6 | Multiple Cloning Sequence in SEQ ID NO. 3<br>GGTACCGGATCCGAATTCCAGCTGCGGCCGCTCTAGA | 37 nucleotides | mRNA Production

Ambion mMessage mMachine (AM1345; Ambion, Tex., USA) is used according to the manufacturer's instructions to generate the mRNA. Linearized pSLU plasmid (1 mg of a stock at a concentration of 0.5-1 mg/ml) is added to a total reaction volume of 20 including 10 ml of ribonucleotides (2×NTP and ARCA:anti-reverse cap analog), 2 ml of 10×T7 reaction buffer, and 2 ml of T7 enzyme and RNase-free water. The reagents are mixed thoroughly, centrifuged briefly to collect the reactants together and incubated at 37° C. for 2-2.5 hours. At this point the DNA template can be digested with DNase, but we have not found this necessary. The RNA is then tailed using E-PAP according to the manufacturer's directions, for 45 min, and then recovered by lithium chloride precipitation and phenol:chloroform extraction and isopropanol precipitation. 40-50 mg of RNA is a typical yield from a 20 ml reaction.

Explant Electroporation

The mRNA is centrifuged for 15,000×g for 6-8 minutes, and the supernatant removed. The pelleted mRNA is washed once in 80% RNA grade ethanol and resuspended in 21 ml RNase free water and incubated at 68-72° C. for 2-3 minutes to dissolve the pellet. Use 1 ml to check the concentration (should be between 2 and 3 mg/ml. The RNA should be kept on ice until ready to use. At this point, if co-transfection is desired, two or more mRNAs can be mixed together. To make the final electroporation mix, use 20 ml of mRNA (or 10 ml of each for two mRNAs), and dilute in water to 0.4-0.8 mg/ml in 50% glycerol-2×PBS so that the final is: 0.8 mg of RNA/10% glycerol in 1×PBS with 1 ml RNase inhibitor. Put the explants in the electroporation chamber and fill with HBSS; the positive electrode below the explant and the negative electrode above. Add the RNA solution carefully over the explant, such that it sinks and rests on top. Then apply the voltage: 10 Volts, 55 msec, 3 pulses is optimum for our tissues, but other tissues may require different settings that need to be empirically derived. The explants are then returned to the tissue culture medium for up to 36 hrs.

Cell Line Transfection

For transfection of cell lines, 24-well TC plates were coated with poly-D-Lysine for 30 minutes and then rinsed well with water 3-5 times. HEK-293 and rat Muller cell line cells were plated in DMEM-F12 media with 10% fetal bovine serum and penicillin/streptomycin. 2 hours prior to transfection, media was changed to Optimem media without antibiotics. TRANS-IT/FUGENE® (Roche)/GENEJAMMER® (Agilent) was mixed with the RNA in a 3:1 ratio (3 ul/1 ug) and allowed for mix for 20 minutes and then added to the wells. The plates were then returned to incubator and GFP expression analyzed 24 hours later.

Figure 2:
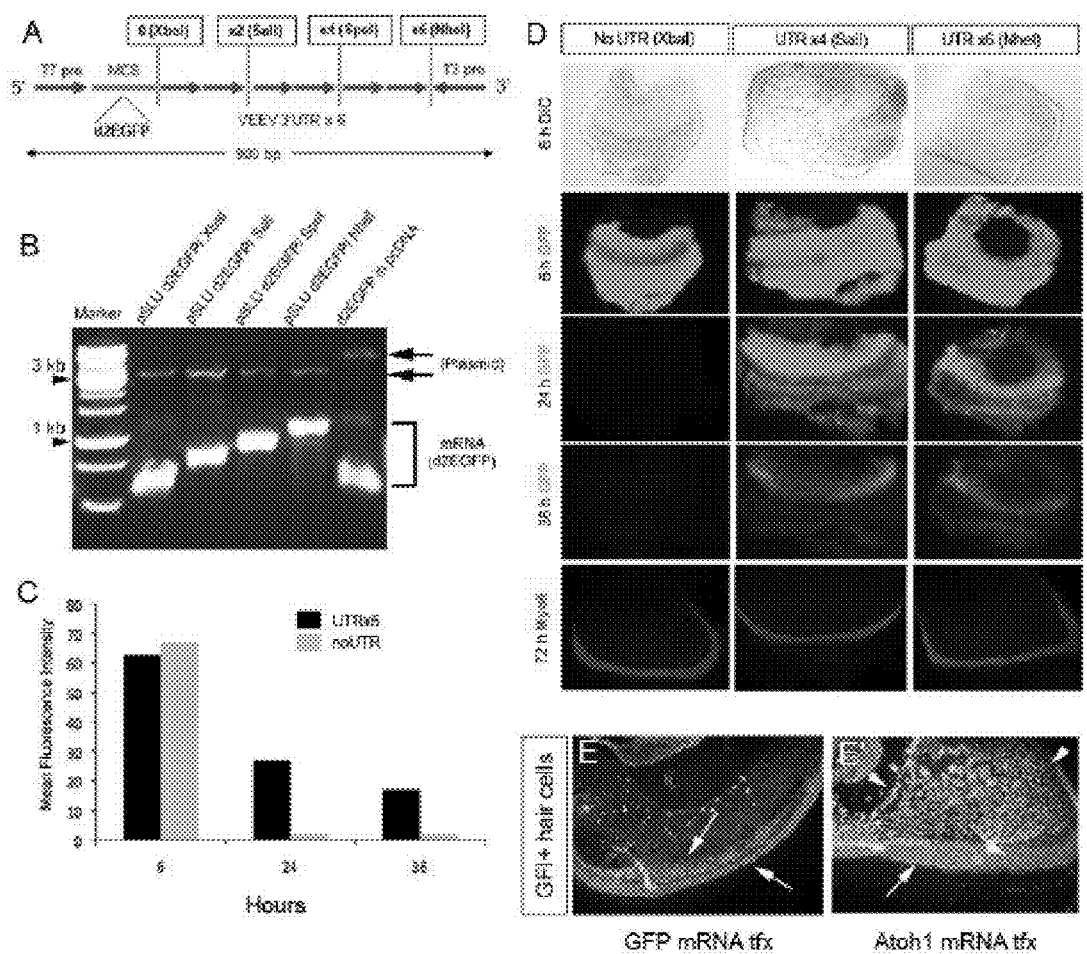
FIGS. 2A-2E' illustrate embodiments of pSLU plasmids incorporating sequences from the Venezuelan equine encephalitis virus (VEEV) 3'-untranslated region (3'UTR)

We tested whether incorporating these sequences from the 3' UTR of the Venezuelan equine encephalitis virus (VEEV) or the Sinbis virus could be useful for stabilizing the mRNA. We first tested a single repeat and found this was not effective when taken from either the Sinbis virus (300 bp) or the VEEV virus (100 bp). However, since the VEEV sequence was only 100 bp long, we generated multimers of the sequence and tested whether multimers of this sequence would be more effective than the monomers. We found that 2 or more repeats of the sequence at the 3' end of the transcript would stabilize the message and allow expression for up to 24 hours (FIG. 2 D,E). When 4 or 6 repeats of the sequence were used the destabilized eGFP expression was observed as long as 36 hours (FIG. 2 B-D and FIG. 10). We call this technique the StabiLized UTR approach, or SLU. We designed a plasmid for cloning genes with varying numbers of repeats of the stabilizing sequences, called pSLU.

Figure 3:
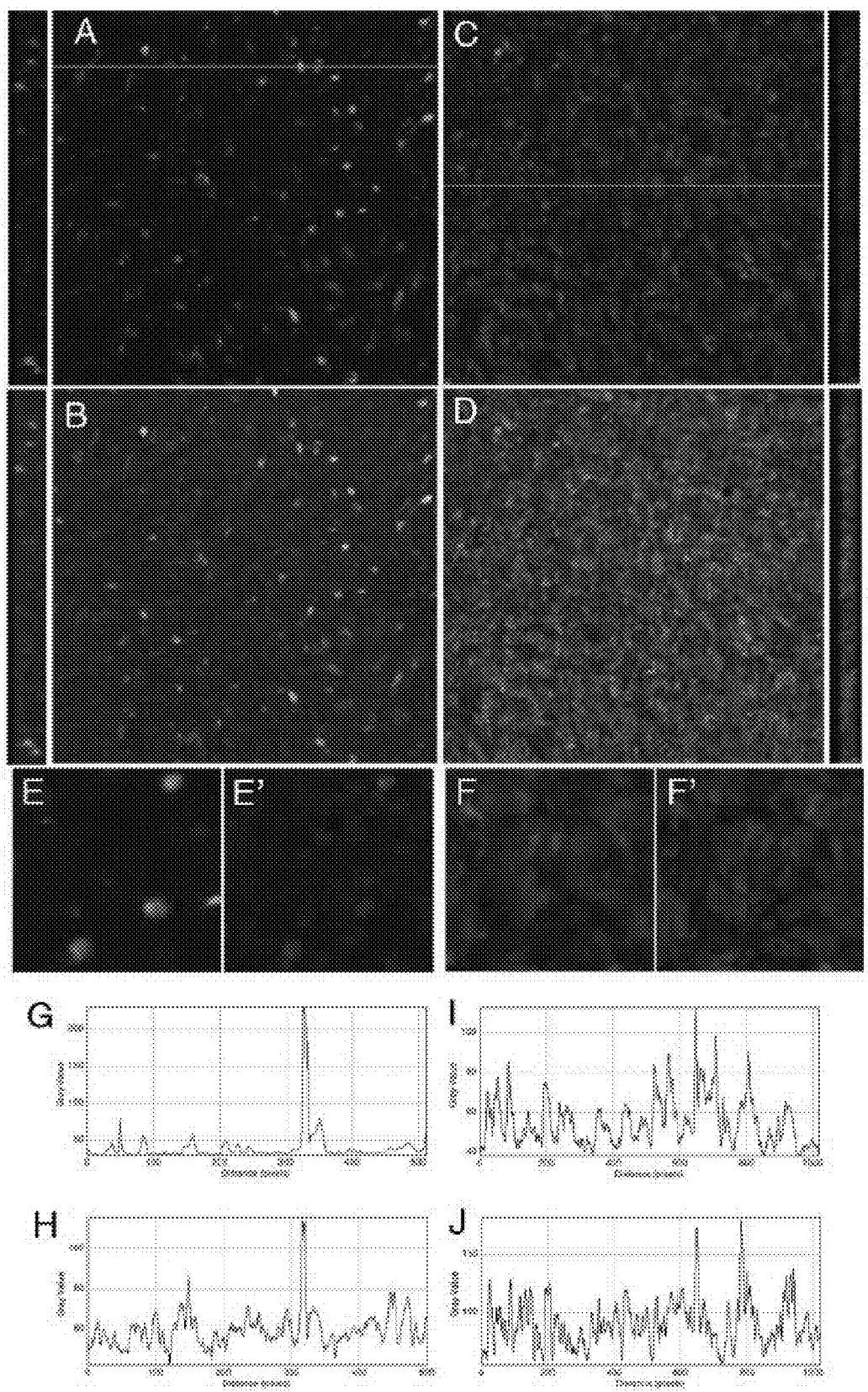
Figure 4:
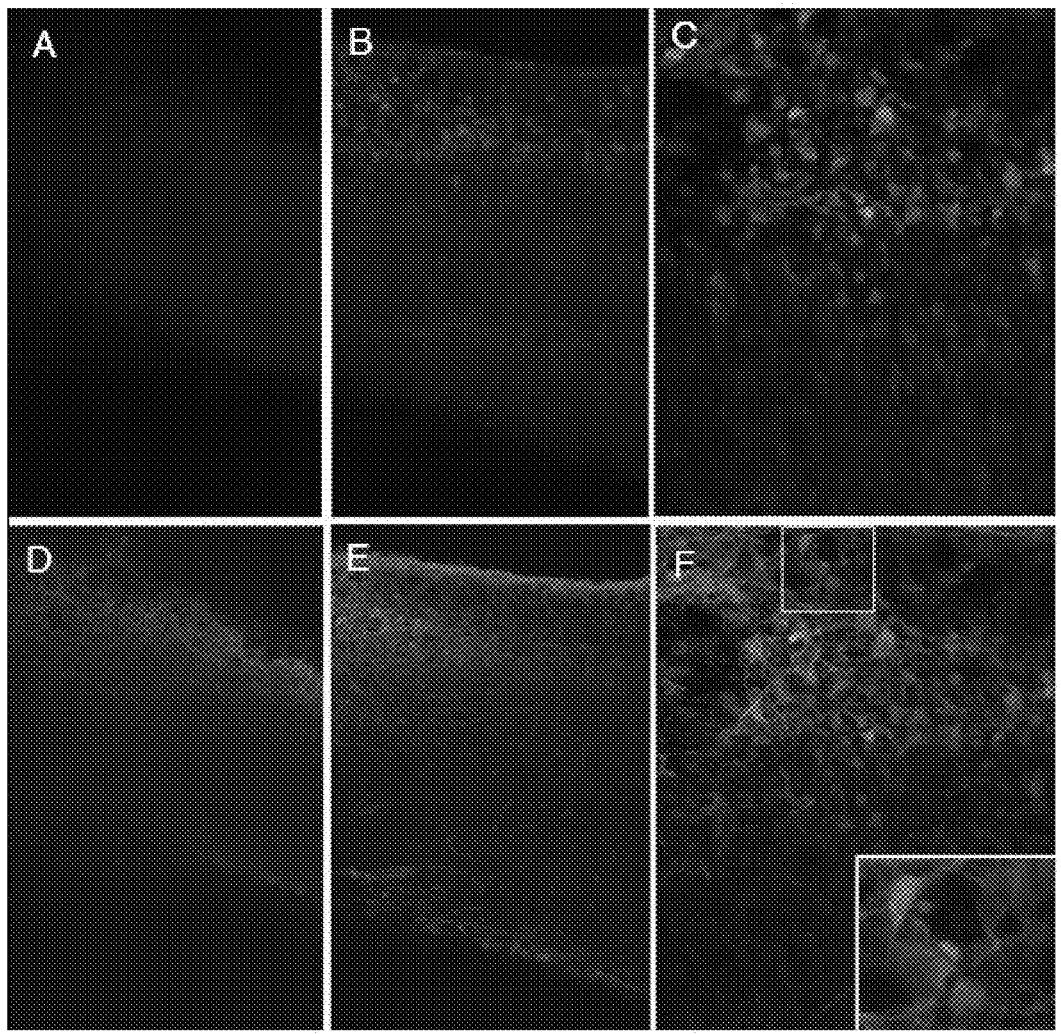
Figure 5:
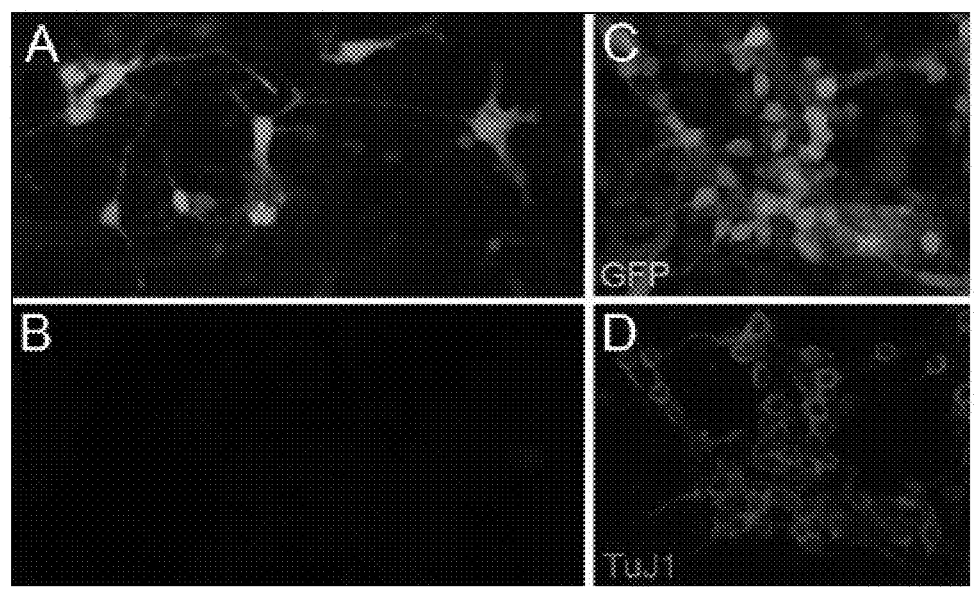

In addition to GFP, we tested several other constructs to determine whether transient expression of proteins could reach functional levels within this time-frame. Over-expression of Atoh1, a gene that is necessary and sufficient for cochlear hair cell development[14-16], shows that stabilized mRNA is significantly more efficient than plasmid DNA, with large number of hair cells in the GER (FIG. 2E,E'). Thus, the method allows for a high level of rapid expression of genes that can act as developmental switches like transcription factors. In this case, a relatively short pulse of Atoh1 was sufficient to direct the GER cells to the stable hair cell fate. In addition to the cochlea, we tested this method on a variety of other tissues and cells. We transfected mRNA coding for the transcription factor Ascl1 into the embryonic retina and assayed its expression (FIG. 3). We found that the levels of Ascl1 expression in the retina from the mRNA produced from the pSLU with six repeats was very evenly expressed throughout all cells, in contrast to the plasmid encoding the same gene. We found that mRNA generated from the pSLU plasmid drove GFP expression in neurons derived from human ES cells (FIG. 4) or mouse cerebral cortex (FIG. 5), both of which have been relatively difficult to transfect with other methods, and can require specialized promoters for robust expression from plasmid transfections. The same technique works well with cell lines (HEK—FIG. 6—and an immortalized Muller glial line—FIG. 7) that are transfected with various lipid-based transfection methods, and so should have wide applicability.

The SLU technique will allow studies of the effects of transient mis-expression to be carried out much more efficiently than existing systems. The length of time for mis-expression can be determined by the number of VEEV sequences incorporated into the gene of interest. Most existing gene mis-expression approaches do not allow control over the timing of expression. Although transfection with Dox regulated genes in plasmids allows a good degree of control of timing, this approach has the disadvantage that additional small molecule regulators need to be added to the system and the effects of these on the developmental process must be controlled for. In addition, the efficiency of expression from cell-specific promoters and of regulated expression must be optimized for each developmental system.

Our data showing that only a transient expression of Atoh1 is sufficient to drive the GER cells to a hair cell fate is characteristic of the types of studies that could be done with this system. Frequently in development, transcription factors act as stable "on" switches in the logic of developmental circuits.

Atoh1 is an example of this type of sustained "on" switch, since after a relatively brief period of development it is not longer required. The use of highly transient mis-expression system like that which we have described will be very useful in identifying which transcriptional regulators act in this manner and to better define the specific windows of developmental time over which these factors act. The SLU technique may also have advantages over other approaches for gene expression in cells in a way that does not permanently modify the genome. For example, when creating iPS cells, methods that allow efficient expression of pluripotency factors to reprogram cells that do not use viruses are desirable, and the SLU method may find applicability in this area.

In summary, we have developed a way to stabilize mRNA for up to 36 hours in cells, sufficient time for analysis of effects of gene mis-expression in many experiments. This will allow investigators to better take advantage of the benefits of mRNA over other gene mis-expression approaches, including the rapid, highly efficient, and widespread mis-expression that is not limited to specific cell types.

CONCLUSION

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while process steps or functions are presented in a given order, alternative embodiments may perform functions in a different order, or functions may be performed substantially concurrently. The teachings of the disclosure provided herein can be applied to other systems, not only the system described herein. The various embodiments described herein can be combined to provide further embodiments.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. Accordingly, the disclosure is not limited, except as by the appended claims.

REFERENCES

The following references are herein incorporated by reference.

1. W. A. Keown, C. R. Campbell, and R. S. Kucherlapati, *Methods Enzymol* 185, 527 (1990).
2. R. C. Mulligan and P. Berg, *Mol Cell Biol* 1 (5), 449 (1981).
3. R. C. Mulligan and P. Berg, *Science* 209 (4463), 1422 (1980).
4. T. Itani, H. Ariga, N. Yamaguchi et al., *Gene* 56 (2-3), 267 (1987).
5. M. Zeitelhofer, J. P. Vessey, S. Thomas et al., *Curr Protoc Neurosci* Chapter 4, Unit 4 32 (2009).
6. A. Gartner, L. Collin, and G. Lalli, *Methods Enzymol* 406, 374 (2006).
7. M. U. Ehrengruber and K. Lundstrom, *Curr Protoc Neurosci* Chapter 4, Unit 4 22 (2007).
8. M. U. Ehrengruber and K. Lundstrom, *Curr Protoc Hum Genet* Chapter 12, Unit 12 2 (2002).
9. S. Perri, D. A. Driver, J. P. Gardner et al., *J Virol* 74 (20), 9802 (2000).
10. V. J. Dwarki, R. W. Malone, and I. M. Verma, *Methods Enzymol* 217, 644 (1993).
11. R. W. Malone, P. L. Felgner, and I. M. Verma, *Proc Natl Acad Sci USA* 86 (16), 6077 (1989).
12. T. Mutzke, G. Schubkegel, R. Teufel et al., *Nucleosides Nucleotides Nucleic Acids* 24 (2), 147 (2005).
13. S. Sasagawa, T. Takabatake, Y. Takabatake et al., *Genesis* 33 (2), 81 (2002).
14. N. A. Bermingham, B. A. Hassan, S. D. Price et al., *Science* 284 (5421), 1837 (1999).
15. J. L. Zheng and W. Q. Gao, *Nat Neurosci* 3 (6), 580 (2000).
16. S. P. Gubbels, D. W. Woessner, J. C. Mitchell et al., *Nature* 455 (7212), 537 (2008).

We claim:

1. A recombinant nucleic acid, comprising
   (a) an RNA molecule; and
   (b) a first recombinant RNA comprising two or more copies of a 3' untranslated region (UTR) of an RNA virus selected from the group consisting of Venezuelan equine encephalitis virus (VEEV) and Sinbis virus;
   wherein the first recombinant RNA is coupled to the 3' end of the RNA molecule.

2. The recombinant nucleic acid of claim 1, wherein the first recombinant RNA comprises three or more copies of the 3' UTR.

3. The recombinant nucleic acid of claim 1, wherein the first recombinant RNA comprises six or more copies of the 3' UTR.

4. The recombinant nucleic acid of claim 1, wherein the recombinant RNA comprises an RNA transcript encoded by SEQ ID NO:1.

5. An isolated host cell transfected with the recombinant nucleic acid of claim 1.

6. An isolated host cell transfected with the recombinant nucleic acid of claim 4.

7. A method for RNA transfection, comprising transfecting the recombinant nucleic acid of claim 1 into a host cell.

8. A method for RNA transfection, comprising transfecting the recombinant nucleic acid of claim 4 into a host cell.

9. The recombinant nucleic acid of claim 1, wherein the RNA molecule is selected from the group consisting of an mRNA molecule and an siRNA molecule.

10. An isolated host cell transfected with the recombinant nucleic acid of claim 3.

11. A method for RNA transfection, comprising transfecting the recombinant nucleic acid of claim 3 into a host cell.

12. The recombinant nucleic acid of claim 3, wherein the RNA molecule is selected from the group consisting of an mRNA molecule and an siRNA molecule.

13. The recombinant nucleic acid of claim 4, wherein the RNA molecule is selected from the group consisting of an mRNA molecule and an siRNA molecule.

14. The recombinant nucleic acid of claim 4, wherein the first recombinant RNA comprises six or more copies the 3' UTR.

15. The recombinant nucleic acid of claim 1, wherein the recombinant RNA comprises an RNA transcript encoded by SEQ ID NO:2.

16. The recombinant nucleic acid of claim 15, wherein the first recombinant RNA comprises six or more copies the 3' UTR.

17. An isolated host cell transfected with the recombinant nucleic acid of claim 15.

18. A method for RNA transfection, comprising transfecting the recombinant nucleic acid of claim 15 into a host cell.

19. An isolated host cell transfected with the recombinant nucleic acid of claim 16.

20. A method for RNA transfection, comprising transfecting the recombinant nucleic acid of claim 16 into a host cell.

* * * * *

SEQUENCE LISTING

<160> NUMBER OF SEQ ID NOS: 6

<210> SEQ ID NO 1
<211> LENGTH: 98
<212> TYPE: DNA
<213> ORGANISM: Artificial Sequence
<220> FEATURE:
<223> OTHER INFORMATION: Synthetic

<400> SEQUENCE: 1

```
acatagcagc aattggcaag ctgcttatat agaacttgcg gcgattggca tgccgcttta    60
aaattttatt ttattttctt ttcttttccg aatcggat                            98
```

-continued

```
<210> SEQ ID NO 2
<211> LENGTH: 300
<212> TYPE: DNA
<213> ORGANISM: Artificial Sequence
<220> FEATURE:
<223> OTHER INFORMATION: Synthetic

<400> SEQUENCE: 2
ccgctacgcc ccaatgaccc gaccagcaaa actcgacgta ctaccgagga accgatgtgc      60
ataacgcatc gggctggtac attagatccc cgtcatcaga cgggctcata gcgacgctaa     120
aactcgacgt attcccgagg aagtgcagtg cataatgctg agcagcgtcg tcatatattc     180
acttattatt caatatagag tagacaccaa aactcaatgt atttctgagg aagcgtggtg     240
cataatgcca cgcagtgtct acataatcaa tttattattt ctttttattt tattcacata     300

<210> SEQ ID NO 3
<211> LENGTH: 790
<212> TYPE: DNA
<213> ORGANISM: Artificial Sequence
<220> FEATURE:
<223> OTHER INFORMATION: Synthetic

<400> SEQUENCE: 3
gacgtcgcgt aatacgactc actatagggc gaattggtac cggatccgaa ttccagctgc      60
ggccgctcta gacacgtgac atagcagcaa ttggcaagct gcttatatag aacttgcggc     120
gattggcatg ccgcttttaaa attttatttt attttctttt cttttccgaa tcggatcatc     180
tagtacatag cagcaattgg caagctgctt atatagaact gcggcgatt ggcatgccgc     240 tttaaaattt tattttattt tcttttcttt tccgaatcgg atgatatcaa gcttgtcgac     300
acatagcagc aattggcaag ctgcttatat agaacttgcg gcgattggca tgccgcttta     360 aaatttttatt ttattttctt ttcttttccg aatcggatta gtactacata gcagcaattg     420
gcaagctgct tatatagaac ttgcggcgat tggcatgccg ctttaaaatt ttattttatt     480
ttcttttctt ttccgaatcg gatactagtc atatgtacgt aacatagcag caattggcaa     540
gctgcttata tagaacttgc ggcgattggc atgccgcttt aaaattttat ttatttttct     600
tttcttttcc gaatcggatt atctagtaca tagcagcaat tggcaagctg cttatataga     660
acttgcggcg attggcatgc cgcttttaaaa tttattttta ttttcttttc ttttccgaat     720
cggatcacgt ggctagcaga tctccatggc ccgggttgtt ccctttagtg agggttaatt     780
gcgctggcca                                                            790

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
taatacgact cactataggg c                                                21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ccctttagtg agggttaatt                                                  20
```

```
<210> SEQ ID NO 6
<211> LENGTH: 37
<212> TYPE: DNA
<213> ORGANISM: Artificial Sequence
<220> FEATURE:
<223> OTHER INFORMATION: Synthetic

<400> SEQUENCE: 6
ggtaccggat ccgaattcca gctgcggccg ctctaga                              37
```